United States Patent [19]

McEvily et al.

[11] Patent Number: 5,202,141

[45] Date of Patent: Apr. 13, 1993

[54] COMPOSITIONS AND METHODS FOR INHIBITING BROWNING IN FOODS AND BEVERAGES

[76] Inventors: Arthur J. McEvily, 56 Nonesuch Rd., Weston, Mass. 02193; Radha Iyengar, 43 Flett Rd., Belmont, Mass. 02178; Akiva Gross, 78 Vine St., Newton, Mass. 02167

[21] Appl. No.: 712,794

[22] Filed: Jun. 10, 1991

Related U.S. Application Data

[63] Continuation-in-part of Ser. No. 537,361, Jun. 13, 1990, Pat. No. 5,059,438, which is a continuation-in-part of Ser. No. 475,150, Feb. 5, 1990, abandoned.

[51] Int. Cl.$^5$ .................................................. A23B 7/00
[52] U.S. Cl. ............................... 426/268; 426/331; 426/541; 426/310; 564/170
[58] Field of Search ................ 426/310, 599, 615, 268, 426/269, 321, 323, 326, 333, 263, 327, 332, 376, 643, 654, 658, 541; 564/170

[56] References Cited

U.S. PATENT DOCUMENTS

| | | |
|---|---|---|
| 3,305,366 | 2/1967 | Sutton et al. . |
| 3,337,348 | 8/1967 | White et al. . |
| 3,754,938 | 8/1973 | Ponting . |
| 3,859,450 | 1/1975 | Alsina . |
| 3,982,030 | 9/1976 | Alsina . |
| 4,814,192 | 3/1989 | Sapers et al. . |
| 4,818,549 | 4/1989 | Steiner et al. . |
| 4,900,564 | 2/1990 | Lee et al. . |
| 5,059,438 | 10/1991 | McEvily ........................... 426/268 |

FOREIGN PATENT DOCUMENTS

| | | |
|---|---|---|
| 0275710 | 7/1988 | European Pat. Off. . |
| 341664 | 11/1989 | European Pat. Off. . |
| WO88/02602 | 4/1988 | PCT Int'l Appl. . |
| WO89/11227 | 11/1989 | PCT Int'l Appl. . |

OTHER PUBLICATIONS

J. D. McCord and A. Kilara, *J. of Food Science*, 48:1479-1483 (1983).

J. Zawistowski et al., *Can. Inst. Food Sci. Tech.*, 20:162-165 (1987).
J. R. L. Walker, *Food Technology*, 11:341-345 (1976).
M. B. Faulkner et al., *Advanced Food Research*, 19:302-310 (1953).
T. P. Labuza, *Cereal Foods World*, 34(4):353 (1989).
D. D. Duxbury (Ed.), *Food Processing*, Apr., 1990, p. 44.
T. Labuza, *Seafood Leader*, May/Jun. (1990).
S. H. Kelly and B. J. Finkle, *J. Sci. Fd. Agric.*, 20:629-632 (1969).
J. R. L. Walker and E. L. Wilson, *J. Sci. Fd. Agric.*, 26:1925-1831 (1975).
P. G. Pifferi et al., *J. Sci. Fd. Agric.*, 25:263-270 (1974).
G. M. Sapers et al., *J. Food Science*, 54(4):997-1012 (1989).
M. W. Montgomery, *J. Food Science*, 48:951-952 (1983).
O. J. Ferrer et al., *J. Food Science*, 54(2):478-480 (1989).
R. Singh and T. R. Ahlawat, *J. Food Sci. Tech.*, 10:172-175 (1973).
Enzyme Development Corporation Technical Bulletin, "Prevention of Melanosis in Shrimp with Enzeco® Ficin".

(List continued on next page.)

*Primary Examiner*—Carolyn Paden
*Attorney, Agent, or Firm*—Hamilton, Brook, Smith & Reynolds

[57] ABSTRACT

Compositions and methods are described for preventing or inhibiting oxidative darkening of foods and beverages. The compositions comprise at least one substituted resorcinol derivative and at least one additive which when applied in combination with the resorcinol derivative prevents enzymatic browning of the food or beverage. The compositions inhibit the enzymatic browning of foods and beverages susceptible to browning, such as shrimp, potatoes, apples, avocados, fruit juices and wines.

37 Claims, No Drawings

OTHER PUBLICATIONS

Enzyme Development Corporation Technical Bulletin, "Treatment of Prawns with Enzeco ® Ficin to Prevent Melanosis".

Ponting et al., *J. Food Science*, 37:434-436 (1972).

J. K. Palmer and J. B. Roberts, *Science*, 157:200-201 (1967).

C. T. Shannon and D. E. Pratt, *J. Food Science*, 32:479-483 (1967).

W. S. Otwell and M. Marshall, *In: Proceedings of the Eleventh Annual Tropical and Subtropical Fisheries Conference of the Americas*, pp. 35-44.

H. Heymann et al., *J. Am. Chem. Soc.*, 76:6330-6335 (1954).

G. Schneider and S. Schmidt, *Z. Physiol. Chem.*, 315:20-27 (1959).

D. A. Robb et al., *Phytochemistry*, 5:665-675 (1966).

D. Richter, *Biochem. J.*, 76:901-908 (1934).

Kuttner and Wagreich, *Arch Biochem. Biophys.* 43:80-87 (1952).

Sagi et al., *Acta Alimentaria* 12:143-148 (1983).

COMPOSITIONS AND METHODS FOR INHIBITING BROWNING IN FOODS AND BEVERAGES

RELATED APPLICATIONS

This application is a continuation-in-part of U.S. patent application Ser. No. 07/537,361, filed Jun. 13, 1990 now U.S. Pat. No. 5,059,438, which is a continuation-in-part of U.S. patent application Ser. No. 07/475,150, filed Feb. 5, 1990 now abandoned, the entire disclosures of which are incorporated herein by reference.

BACKGROUND OF THE INVENTION

Browning of foods is a major problem in the food and beverage industry. Browning, or oxidative darkening, can be the result of the action of an enzyme, such as polyphenol oxidase (PPO; also known as tyrosinase), or the result of non-enzymatic chemical reactions, for example, due to polymerization of phenolic compounds which are present in some foods. High PPO activity is present in foods which are susceptible to browning, e.g., shrimp, bananas and mushrooms. Browning causes deleterious changes in the appearance and texture of foods and beverages. Both enzymatic and non-enzymatic browning constitute serious problems for the food industry and result in millions of pounds of wasted food products per year.

Enzymatic browning, in particular, has been the subject of much research, particularly as the causative agent of shrimp melanosis, which is characterize by the formation of dark spots on shrimp. Faulkner et al., *Advanced Food Research*, 19:302-310 (1953). Enzymatic browning is the result of PPO-catalyzed oxidation of mono- and diphenols to o-quinones which polymerize spontaneously to form dark-colored, high molecular weight polymers, leading to the characteristic browning or formation of dark spots.

Several methods have been developed to prevent browning, including heat inactivation of PPO and various chemical treatments, such as altering the pH of the food. Heat inactivation is not appropriate for fresh foods, such as fruits and seafood, as the high temperatures necessary to inactivate PPO change the quality and texture of the foods. Likewise, reducing the pH by adding an acid (e.g., citric acid or phosphoric acid) deleteriously affects the appearance and quality of some foods.

The control of PPO-catalyzed enzymatic browning in mushrooms using citric acid was reported by McCord and Kilara in the *Journal of Food Science*, 48: 1479-1483 (1983). The inhibition of polyphenol oxidase activity in an extract of Jerusalem artichokes using various sulfite compounds was described in Zawistowski et al., in *Can. Inst. Food Sci. Tech. J.*, 20(3):162-164 (1987). The use of cinnamic acid, p-coumaric acid and ferulic acid to control enzymatic browning in fruit juices was described by J. R. L. Walker in *Food Technology*, 11:341-345 (1976). T. C. Wong et al. report in *Plant. Physiol.*, 48:24-30 (1971) that phlorogulcinol and resorcinol, and their derivatives d-catechin and orcinol react with 4-methyl-o-quinone which is formed by PPO in peaches, although these compounds are not substrates for PPO. R. Kuttner and H. Wagreich, *Arch. Biochem. Biophys.*, 43:80-87 (1952) report that mushroom PPO (catecholase) is inhibited by benzoic acid and selected benzoic acid derivatives. None of these methods have proven entirely satisfactory, however, due to expense, lack of availability, or inferior performance.

Labuza in *Cereal Foods World*, 34(4):353 (1989) describes the sue of proteases, especially ficin, in the control of enzymatic browning of certain foods. The author attributed this effect to attack on PPO by the protease.

Another method for reducing browning which has been prevalent in the food industry is adding sulfite salts to foods and beverages. Some forms of enzymatic browning, such as shrimp melanosis, have traditionally been treated by dipping or coating the shrimp or other food in a sulfite solution, such as sodium bisulfite. Sulfites are also added to wines to prevent oxidation. Sulfites reduce o-quinones to the mono- and/or diphenols, thereby inhibiting the browning reaction. However, the use of sulfite in foods has been restricted due to adverse health effects in certain individuals, and may be restricted further or even eliminated completely.

SUMMARY OF THE INVENTION

Compositions and methods are described for preventing or inhibiting oxidative darkening of foods and beverages. The compositions comprise at least one substituted resorcinol derivative and at least one additive which when applied in combination with the resorcinol derivative prevents enzymatic browning of the food or beverage. The additives can be a sulfite-containing compound such as sodium metabisulfite; a mild food grade reducing agent such as ascorbic or erythorbic acids; a food grade organic acid such as citric, fumaric, tartaric or malic acid; a chelating agent such as ethylenediaminetetraacetic acid or sodium acid pyrophosphate; or an inorganic salt such as calcium chloride, sodium chloride, zinc chloride or sodium bicarbonate. Components of the present compositions act in synergy to effectively inhibit browning in selected foods or beverages, without adversely affecting the appearance, taste, texture or quality of the food or beverage.

DETAILED DESCRIPTION OF THE INVENTION

This invention pertains to compositions and methods for inhibiting oxidative browning of foods and beverages, particularly enzymatic browning caused by PPO activity. The invention involves subjecting a food or beverage to a composition comprising at least one substituted resorcinol derivative and at least one additional additive for a period of time sufficient to inhibit enzymatic browning. An additive is a compound which is known to inhibit oxidative browning of certain foods or beverages, or one which when admixed with the substituted resorcinol compounds inhibits enzymatic browning. Additives that can be sued in the composition of this invention include sulfite-containing compounds such as sodium metabisulfite; mild food grade reducing agents such as ascorbic acid, erythorbic acids and derivatives of these such as ascorbyl phosphate and ascorbyl fatty acid esters; food grade acidulents such as citric, fumaric, tartaric, malic acid, etc.; chelating agents such as ethylenediaminetetraacetic acid (EDTA) or sodium acid pyrophosphate; or inorganic salts such as calcium chloride, sodium chloride, zinc chloride or sodium bicarbonate. One or more additives can be used in combination to achieve the desired effect. The compositions may optionally include conventional additives such as emulsifiers, dispersing agents, etc.

It has now been shown that substituted resorcinol derivatives when used in combination with at least one additional additive, act in synergy to inhibit browning in foods and beverages. The degree of inhibition is enhanced when the components are sued in combination, than that observed when each component is individually applied to the food or beverage. Complete prevention of enzymatic browning is difficult to achieve due to the presence of pigment precursors formed prior to the addition of inhibitor or due to browning that is not initiated by PPO catalysis (nonenzymatic browning). However, compositions of this invention can be used to reduce and minimize browning beyond that which is observed when reducing agents alone are used.

Resorcinol derivatives and especially those substituted at the 4-position comprise a class of compounds which are highly effective in inhibiting the activity of the enzyme, polyphenol oxidase, from a number of sources. Preferably, the 4-substituted resorcinols are compounds having the general formula:

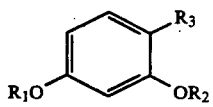

Formula I wherein $R_1$ and $R_2$ are independently selected from the group consisting of H, $CH_3$, COR', CR', $PO_3R'R''$ and $SO_3R'4''$; wherein R' and R'' are independently H or an alkyl group having from 1 to about 6 carbon atoms in a linear, branched or cyclic configuration or a substituted aromatic compound having from about 4 to about 10 carbon atoms; and $R_3$ is an organic or inorganic substituent selected so that the resulting compound is an inhibitor of the enzyme PPO. For example, $R_3$ can be a heteroatom or a group containing a heteroatom, a saturated or unsaturated alkyl group, a substituted aromatic compound or an organic functional group selected so that the compound has inhibitory activity. The heteroatom can include, for example, oxygen (O), nitrogen (N), sulfur (S), phosphorus (P) or halogens such as chlorine (Cl), bromine (Br), iodine (I) or fluorine (F). The saturated or unsaturated alkyl group can have from 1 to 30 carbon atoms in a linear, branched or cyclic configuration and can include a substituted aromatic compound. The alkyl substituents or organic functional groups can contain a heteroatom or heteroatoms, for example, oxygen (O), nitrogen (N), sulfur (S), phosphorus (P) or halogens such as chlorine (Cl), bromine (Br), iodine (I) or fluorine (F).

4-Alkylresorcinol compounds in combination with other additives are particularly effective for inhibiting browning in foods. For example, 4-hexylresorcinol, having the structure shown below (wherein $R_1$ and $R_2$ are both H and $R_3$ is $C_6H_{13}$) has been shown to be highly effective for this purpose.

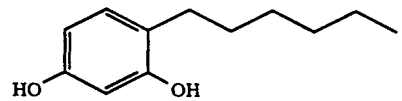

Formula II

In one embodiment, $R_3$ has the general structure:

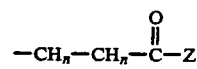

wherein n is 1 or 2 and Z is an alkyl or other organic functional group selected so that the compound has inhibitory activity. Z can be an alkyl substituent containing at least one heteroatom, such as oxygen (O), nitrogen (N), sulfur (S), phosphorus (P) or halogens such as chlorine (Cl), bromine (Br), iodine (I) or fluorine (F). In a preferred embodiment, Z is selected from the group consisting of OH, $NH_2$, $O(CH_2)_xCH_3$, $NHCO_2(CH_2)_xCH_3$, $NH(CH_2)_xCH_3$, amino acids, polyamine metabolites, such as $NH(CH_2)_xNH_2$, $NH(CH_2)_xNH(CH_2)_yNH_2$, $NH(CH_2)_xNHR_4$, $NH(CH_2)_xNH(CH_2)_yNHR_4$ wherein x and y independently can be any integer from 0 to 5; and higher polyamine oligomers or substituted oligomers conisting of at least three monomers, wherein the monomer is a 1,ω-diaminoalkane and $R_4$ has the following formula:

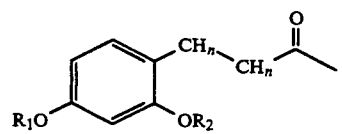

wherein n, $R_1$ and $R_2$ are defined above. Compounds which are particularly effective inhibitors of oxidative browning are resorcinol derivatives having the general formula:

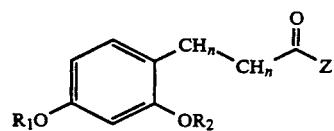

Formula III wherein n is 1 or 2 and $R_1$ and $R_2$ and Z are as defined above.

Particularly useful resorcinol derivatives for inhibiting enzymatic browning are obtained when n=2, $R_1$ and $R_2$ are both H and Z is OH, $NH(CH_2)_4NH_2$, $NH(CH_2)_4NHR_4$ (where x=4) or $NH(CH_2)_4NH(CH_2)_3NHR_4$ (where x=4, y=3 and $R_4$ is as defined above). These compounds are shown as Formulae IV, V, VI and VII respectively:

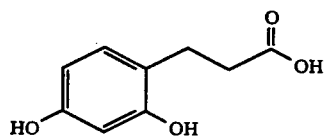

Formula IV

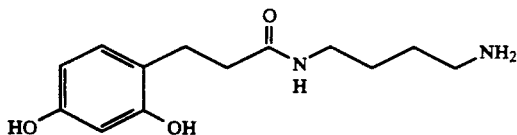

Formula V

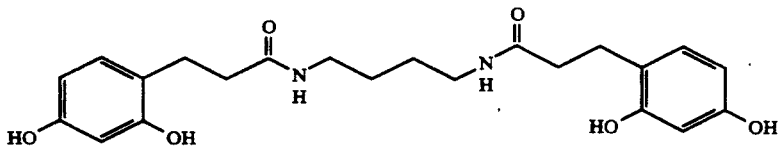

Formula VI

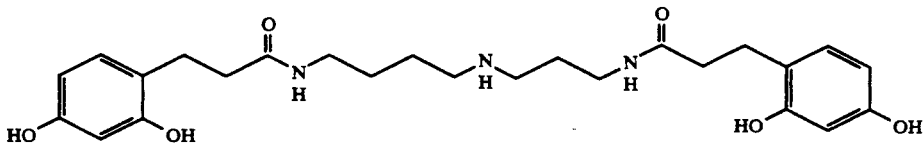

Formula VII

The invention includes functional equivalents of these formulae (Formulae I–VII). The term "functional equivalents" means a chemical derivative or analog of the compound which has similar anti-browning activity. As used herein, a molecule is said to be a "derivative" of another molecule when it contains additional or different chemical moieties not normally part of the molecule. Specific resorcinol compounds and their synthesis are described in detail in U.S. Ser. No. 07/537,361, filed Jun. 13, 1990.

Low concentrations of the resorcinol derivatives reduce the level of enzymatic browning but will not completely prevent the nonenzymatic browning of foods due to the presence of pigment precursors prior to the addition of the inhibitor. Increasing the concentration of the resorcinol derivative does not affect the nonenzymatic component of browning. Non-enzymatic browning can be prevented by the addition of high concentrations of reducing agents such as sulfite, ascorbic acid, erythorbic acid, etc., which are known to react chemically with the pigment precursors and the products of ongoing PPO catalysis; however, the effectiveness of the reductants diminishes with time as they are consumed. The 4-substituted resorcinol compounds have been found to be synergistic with other agents such as reducing agents, acidulants, etc., that is the combination of the two types of agents are more effective than either agent individually, even if used at much higher concentrations. The synergistic mixture is used in an amount or concentration sufficient to inhibit or prevent browning. The form of treatment will depend upon the food or beverage being treated and the results sought, and can include, e.g., dipping, spraying, dusting, sprinkling, immersing, mixing and/or soaking. The mixture can be added to an aqueous diluent, for example water, salt water or buffer, and applied to the food, or can be added neat, e.g., to fruit juice or wine. The amount needed will depend upon the susceptibility of the food or beverage, to browning, the condition of the food or beverage and the storage conditions. The amount sufficient to prevent or inhibit browning can be determine empirically by one skilled in the food art. Compositions comprising about 0.01% to 5% by weight of the additive and about 0.001% to 0.5% by weight of the resorcinol derivative will be particularly effective for this purpose.

Foods which are susceptible to browning include certain shellfish, crustaceans, fruits (e.g., apples, avocados, bananas, peaches) vegetables (e.g., potatoes, lettuce) and beverages, such as fruit juices and wines are treated with a composition containing an amount of the present resorcinol derivatives in combination with at least one other anti-browning agent. The amount applied to the food should be sufficient to inhibit the browning reaction. Browning is "prevented" if it is completely eliminated. Browning is "significantly inhibited" if browning takes place at a significantly lower rate compared to untreated foods in the same time frame. Components of the present compositions are non-toxic in levels used and act in synergy to effectively inhibit or prevent browning in selected foods and beverages, without adversely affecting the appearance, taste, texture or quality of the food of beverage.

The invention will be further illustrated by the following non-limiting examples:

EXAMPLES

Example 1

Inhibition of Browning of Apples Using Formula II and Bisulfite

Fresh, whole, McIntosh apples, held at ambient temperature (22° to 24° C.) were sliced by cutting ¼ inch (top to bottom) sections from several apples. The outermost and core sections were discarded. The freshly cut slices were halved (top to bottom) and placed (2–3 slices) in each test solution. The samples were agitated during the soak time to ensure complete contact. After one minute, the slices were removed and placed in clear plastic containers and allowed to stand at ambient temperature and were exposed to air. The apple slices were visually inspected after 1 and 24 hours. The results are shown in Table 1.

TABLE 1

| Test Solution (%, w/v) | 1 Hour | 24 Hours |
|---|---|---|
| Water | browning | browned |
| Formula II (0.05 or 0.1) | white | white with core area browning |
| Formula II (0.05) + bisulfite (0.05) | white | white |
| Formula II (0.01) | white | browning, veins noticeable |
| Bisulfite (0.01) | some browning | browned |
| Formula II (0.01) + bisulfite | white | slight |

TABLE 1-continued

| Test Solution (%, w/v) | 1 Hour | 24 Hours |
| --- | --- | --- |
| (0.01) | | browning near edges |

Example 2

Inhibition of Browning in Apples Using Formula IV and Bisulfite

McIntosh apples were treated and evaluated as described in Example 1. The results are shown below in Table 2.

TABLE 2

| Test Solution (%, w/v) | 1 Hour | 24 Hours |
| --- | --- | --- |
| Water | browning | browned |
| Formula IV (0.2) | white | white |
| Formula IV (0.01) | slight core browning | slight core browning |
| Bisulfite (0.01) | some browning | browned |
| Formula IV (0.01) + bisulfite (0.01) | white | slight browning veins noticeable |

Example 3

Inhibition of Browning in Apples Using Formula IV and Acidulants and/or Reducing Agents McIntosh apples were treated and evaluated as described in Example 1. The results are shown below in Table 3.

TABLE 3

| Test Solution (%, w/v) | 1 Hour | 24 Hours |
| --- | --- | --- |
| Water | browning | browned |
| Formula IV (0.2) | white | veins noticeable |
| Formula IV (0.05) | white | moderate browning |
| Formula IV (0.01) | very slight browning | browned |
| Ascorbic Acid (0.05 or 1.0) | core browned | browned |
| Formula IV (0.05) + Ascorbic Acid (0.5) | white | white |
| Citric Acid (0.5) | white | browned |
| Formula IV (0.05) + Citric Acid (0.5) | white | slight browning |
| Erythorbic Acid (0.5) | white | moderate browning |
| Formula IV (0.05) + Erythorbic Acid (0.5) | white | white |
| Malic Acid (0.5) | white | browned |
| Formula IV (0.05) + Malic Acid (0.5) | very slight browning | moderate browning |
| Malonic Acid (0.5) | white | browned |
| Formula IV (0.05) + Malonic Acid (0.5) | white | moderate browning |

Example 4

Inhibition of Browning in Apples Using Formula IV, Sulfites and Ascorbic Acid

McIntosh apples were treated and evaluated as described in Example 1. The results are shown below in Table 4.

TABLE 4

| Test Solution (%, w/v) | 1 Hour | 24 Hours |
| --- | --- | --- |
| Water | browning | browned |
| Formula IV (0.01) | slight core browning | browning, veins noticeable |
| Bisulfite (0.01) | some browning | browned |
| Ascorbic Acid (0.1) | slight browning | browned |
| Ascorbic Acid (0.5) | white | slight browning |
| Formula IV (0.01) + Bisulfite (0.01) + Ascorbic Acid (0.1) | white | white |
| Formula IV (0.01) + Bisulfite (0.01) + Ascorbic Acid (0.5) | white | white |
| Formula IV (0.01) + Bisulfite (0.05) + Ascorbic Acid (0.5) | white | white |
| Formula IV (0.05) + Bisulfite (0.05) + Ascorbic Acid (0.5) | white | white |

Example 5

Inhibition of Browning of Potatoes Using Formula II and Sulfites

Whole brown russet potatoes were peeled under water. Slices were made by cutting ¼ inch sections from several peeled potatoes. Slices from the ends of the potato were discarded. The remaining freshly cut slices were placed (2-3 slices) in each test solution. The samples were agitated during the soak time to ensure complete contact. After one minute, the slices were removed and placed in clear plastic containers and allowed to stand at ambient temperature and were exposed to air. The potato slices were visually inspected after 1 and 24 hours. The results are shown in Table 5.

TABLE 5

| Test Solution (%, w/v) | 1 Hour | 24 Hours |
| --- | --- | --- |
| Water | reddening | blackened |
| Formula II (0.05) | off colored | slightly browned vascular ring |
| Bisulfite (0.05) | white | slightly browned from edge |
| Bisulfite (0.01) | slight reddening | browned |
| Formula II (0.01) + Bisulfite (0.01) | white | browned near edge |

Example 6

Inhibition of Browning of Potatoes Using Formula IV and Bisulfite

Brown russet potatoes were treated and evaluated as described in Example 5 and the results are shown in Table 6 below.

TABLE 6

| Test Solution (%, w/v) | 1 Hour | 24 Hours |
| --- | --- | --- |
| Water | reddening | blackened |
| Formula IV (0.1) | white | browned |
| Formula IV (0.05) | slight reddening | browned |
| Bisulfite (0.05) | white | browned vascular ring |
| Formula IV (0.05) + Bisulfite (0.05) | white | white |
| Formula IV (0.01) | slight | browned |

TABLE 6-continued

| Test Solution (%, w/v) | 1 Hour | 24 Hours |
| --- | --- | --- |
| Bisulfite (0.01) | browning slight browning | browned |
| Formula IV (0.01) + Bisulfite (0.01) | white | browned near edges |

Example 7

Inhibition of Browning of Potatoes Using Formula IV and Acidulants and/or Reducing Agents Brown russet potatoes were treated and evaluated as described in Example 5 and the results are shown in Table 7.

TABLE 7

| Test Solution (%, w/v) | 1 Hour | 24 Hours |
| --- | --- | --- |
| Water | reddish | blackened |
| Formula IV (0.2) | white | browned vascular ring |
| Formula IV (0.05) | off-colored | some browning |
| Formula IV (0.01) | slight browning | browned |
| Ascorbic Acid (0.5) | red near edges | blackened |
| Ascorbic Acid (0.1) | reddish | browned |
| Formula IV (0.05) + Ascorbic Acid (0.5) | white | very slight browning |
| Citric Acid (0.5 or 1.0) | white | some browning |
| Formula IV (0.05) + Citric Acid (0.5) | white | very slight browning |
| Erythorbic Acid (0.5 or 1.0) | red near edges | blackened |
| Formula IV (0.05) + Erythorbic Acid (0.5) | white | slight browning |
| Malic Acid (0.5) | white | some browning |
| Formula IV (0.05) + Malic Acid (0.5) | white | some browning |
| Malonic Acid (0.5) | white | some browning |
| Formula IV (0.05) + Malonic Acid (0.5) | white | very slight browning |

Example 8

Inhibition of Browning of Potatoes Using Formula IV and Sulfites and Acidulants

Brown russet potatoes were treated and evaluated as described in Example 5. The results are provided in Table 8.

TABLE 8

| Test Solution (%, w/v) | 1 Hour | 24 Hours |
| --- | --- | --- |
| Water | reddening | blackened |
| Formula IV (0.01) | very slight reddening | browned |
| Bisulfite (0.01) | very slight reddening | browned |
| Ascorbic Acid (0.01) | reddening | browned |
| Ascorbic Acid (0.5) | white | slight browning |
| Formula IV (0.01) + Bisulfite (0.01) + Ascorbic Acid (0.1) | very slight reddening | some browning |
| Formula IV (0.01) + Bisulfite (0.01) + Ascorbic Acid (0.5) | white | some browning on edges |
| Formula IV (0.01) + Bisulfite (0.05) + Ascorbic Acid (0.5) | white | white |
| Formula IV (0.01) + Bisulfite | white | white |

TABLE 8-continued

| Test Solution (%, w/v) | 1 Hour | 24 Hours |
| --- | --- | --- |
| (0.05) + Ascorbic Acid (0.5) | | |

Equivalents

Those skilled in the art will recognize, or be able to ascertain, using no more than routine experimentation, many equivalents to the specific embodiments of the invention described herein. Such equivalents are intended to be encompassed by the following claims:

We claim:

1. A method for inhibiting enzymatic browning of foods or beverages susceptible to such browning, comprising applying to the foods or beverages a composition comprising at least one substituted resorcinol derivative and at least one additive selected from the group consisting of a reducing agent, a chelating agent, an acidulant, an inorganic salt and combinations thereof, the amount of additive and resorcinol derivative being sufficient to inhibit browning of the foods, wherein the resorcinol derivative has the following formula:

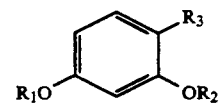

wherein $R_1$ and $R_2$ are independently selected from the group consisting of H, $CH_3$, COR', CR', $PO_3R'R''$ and $SO_3R'R''$ wherein R' and R" are independently H or an alkyl group having from 1 to 6 carbon atoms in a linear, branched or cyclic configuration or a substituted aromatic compound; and wherein $R_3$ is selected so that the resorcinol derivative inhibits enzymatic browning.

2. A method of claim 1, wherein the foods or beverages are selected from the group consisting of crustaceans, shellfish, fruits, vegetables, fruit juices and wines.

3. A method of claim 1, wherein the amount of additive is from about 0.001 to about 5 percent by weight and the amount of resorcinol derivative is from about 0.001 to 0.5 percent by weight.

4. A method of claim 3, wherein the composition is dissolved in an aqueous medium to form an aqueous solution.

5. A method of claim 1, wherein the reducing agent is ascorbic acid, erythorbic acid, sulfiting agents or derivatives of these.

6. A method of claim 1, wherein the acidulant is any food grade acid such as citric acid, fumaric acid, tartaric acid or malic acid.

7. A method of claim 1, wherein the inorganic salt is calcium chloride, sodium chloride, zinc chloride or sodium bicarbonate.

8. A method of claim 1, wherein the chelating agent is ethylenediaminetetraacetic acid or sodium acid pyrophosphate.

9. A method of claim 1, wherein $R_3$ comprises a heteroatom, a saturated or unsaturated alkyl group, a substituted aromatic group or an organic functional group containing a heteroatom.

10. A method of claim 1, wherein $R_3$ comprises at least one heteroatom which is selected from the group consisting of oxygen, nitrogen, sulfur and phosphorus.

11. A method of claim 1, wherein $R_3$ is a saturated or unsaturated alkyl group having from about 1 to about 30 carbon atoms in a linear, branched or cyclic configuration.

12. A method of claim 1, wherein $R_1$ and $R_2$ are both H.

13. A method for inhibiting enzymatic browning of foods or beverages susceptible to such browning, comprising applying to the foods or beverages a composition comprising at least one substituted resorcinol derivative and at least one additive selected from the group consisting of a reducing agent, a chelating agent, an acidulant, an inorganic salt and combinations thereof, the amount of additive and resorcinol derivative being sufficient to inhibit browning of foods, wherein the resorcinol derivative has the following formula:

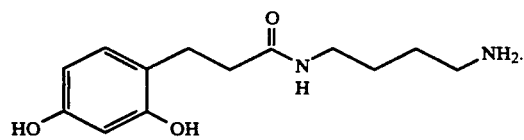

17. A method of claim 14, wherein the resorcinol derivative has the following formula:

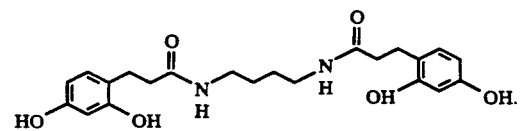

18. A method of claim 14, wherein the resorcinol derivative has the following formula:

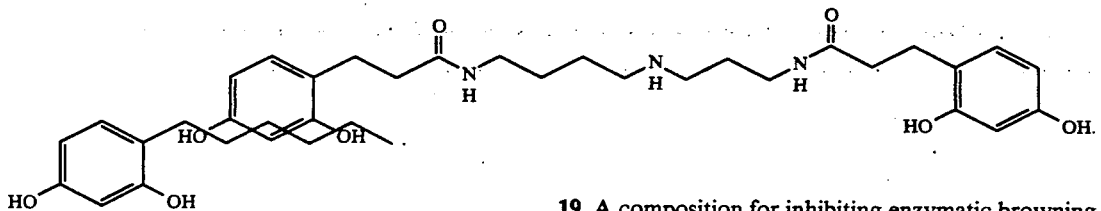

14. A method for inhibiting enzymatic browning of foods or beverages susceptible to such browning, comprising applying to the foods or beverages a composition comprising at least one substituted resorcinol derivative and at least one additive selected from the group consisting of a reducing agent, a chelating agent, an acidulant, an inorganic salt and combinations thereof, the amount of additive and resorcinol derivative being sufficient to inhibit browning of foods, wherein the resorcinol derivative has the following formula:

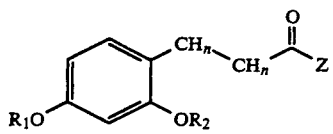

wherein n is 1 or 2; $R_1$ and $R_2$ are independently selected from the group consisting of H, $CH_3$, $COR'$, $CR'$, $PO_3R'R''$ and $SO_3R'R''$ wherein $R'$ and $R''$ are independently H, an alkyl group having from about 1 to about 6 carbon atoms in a linear, branched or cyclic configuration or a substituted aromatic compound; and Z is an OH group, an alkyl or organic functional group selected so that the resorcinol derivative inhibits enzymatic browning.

15. A method of claim 14, wherein the resorcinol derivative has the following formula:

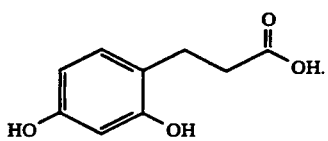

16. A method of claim 14, wherein the resorcinol derivative has the formula:

19. A composition for inhibiting enzymatic browning of foods or beverages susceptible to such browning, comprising at least one substituted resorcinol derivative and at least one additive selected from the group consisting of a reducing agent, a sulfite, a chelating agent, an acidulant, an inorganic salt and combinations thereof, the amount of additive and resorcinol derivative being sufficient to inhibit browning of the foods, wherein the resorcinol derivative has the following formula:

$$\underset{R_1O}{\overset{R_3}{\text{[structure]}}} OR_2$$

wherein $R_1$ and $R_2$ are independently selected from the group consisting of H, $CH_3$, $COR'$, $CR'$, $PO_3R'R''$ and $SO_3R'R''$ wherein $R'$ and $R''$ are independently H or an alkyl group having from 1 to 6 carbon atoms in a linear branched or cyclic configuration or a substituted aromatic compound; and wherein $R_3$ is selected so that the resorcinol derivative inhibits enzymatic browning.

20. A method of claim 19, wherein the amount of additive is from about 0.001 to about 5 percent by weight and the amount of resorcinol derivative is from about 0.001 to 0.5 percent by weight.

21. A method of claim 20, wherein the composition is dissolved in an aqueous medium to form an aqueous solution.

22. A method of claim 19, wherein the reducing agent is ascorbic acid, erythorbic acid, sulfiting agents or derivatives of these.

23. A method of claim 19, wherein the acidulant is any food grade acid such as citric acid, fumaric acid, tartaric acid or malic acid.

24. A method of claim 19, wherein the inorganic salt is calcium chloride, sodium chloride, zinc chloride or sodium bicarbonate.

25. A method of claim 19, wherein the chelating agent is ethylenediaminetetraacetic acid or sodium acid pyrophosphate.

26. A method of claim 19, wherein $R_3$ comprises a heteroatom, a saturated or unsaturated alkyl group, a substituted aromatic group or an organic functional group containing a heteroatom.

27. A method of claim 19, wherein $R_3$ comprises at least one heteroatom which is selected from the group consisting of oxygen, nitrogen, sulfur and phosphorus.

28. A method of claim 19, wherein $R_3$ is a saturated or unsaturated alkyl group having from about 1 to about 30 carbon atoms in a linear, branched or cyclic configuration.

29. A method of claim 19, wherein $R_1$ and $R_2$ are both H.

30. A composition for inhibiting enzymatic browning of foods or beverages susceptible to such browning, comprising at least one substituted resorcinol derivative and at least one additive selected from the group consisting of a reducing agent, a chelating agent, an acidulant, an inorganic salt and combinations thereof, the amount of additive and resorcinol derivative being sufficient to inhibit browning of the foods, wherein the resorcinol derivative has the following formula:

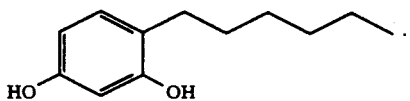

31. A composition of claim 30, wherein the resorcinol derivative has the following formula:

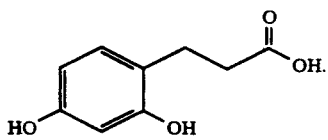

32. A composition of claim 30, wherein the resorcinol derivative has the following formula:

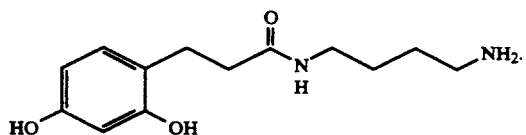

33. A composition of claim 30, wherein the resorcinol derivative has the following formula:

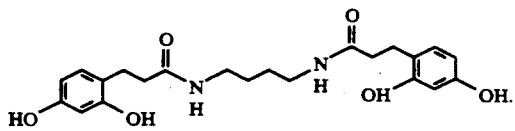

34. A composition of claim 30, wherein the resorcinol derivative has the following formula:

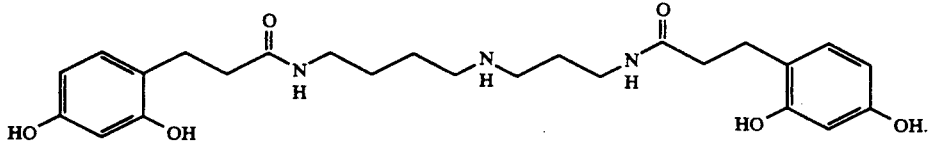

35. A composition for inhibiting enzymatic browning of foods or beverages susceptible to such browning, comprising at least one substituted resorcinol derivative and at least one additive selected from the group consisting of a reducing agent, a chelating agent, an acidulant, an inorganic salt and combinations thereof, the amount of additive and resorcinol derivative being sufficient to inhibit browning of the foods, wherein the resorcinol derivative has the following formula:

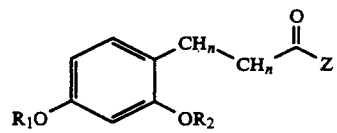

wherein n is 1 or 2; $R_1$ and $R_2$ are independently selected from the group consisting of H, $CH_3$, $COR'$, $CR'$, $PO_3R'R''$ and $SO_3R'R''$ wherein $R'$ and $R''$ are independently H, an alkyl group having from about 1 to about 6 carbon atoms in a linear, branched or cyclic configuration or a substituted aromatic compound; and Z is an OH group, an alkyl or organic functional group selected so that the resorcinol derivative inhibits enzymatic browning.

36. A food or beverage susceptible to enzymatic browning which has been treated with a composition for inhibiting enzymatic browning of foods or beverages susceptible to such browning, comprising at least one substituted resorcinol derivative and at least one additive selected from the group consisting of a reducing agent, a sulfite, a chelating agent, an acidulant, an inorganic salt and combinations thereof, the amount of additive and resorcinol derivative being sufficient to inhibit browning of the foods, wherein the resorcinol derivative has the following formula:

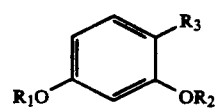

wherein $R_1$ and $R_2$ are independently selected from the group consisting of H, $CH_3$, $COR'$, $CR'$, $PO_3R'R''$ and $SO_3R'R''$ wherein $R'$ and $R''$ are independently H, an alkyl group having from about 1 to about 6 carbon atoms in a linear, branched or cyclic configuration or a substituted aromatic compound; and wherein $R_3$ is selected so that the resorcinol derivative prevents or inhibits enzymatic browning of the food or beverage.

37. A food or beverage susceptible to enzymatic browning of claim 36, wherein the composition comprises a resorcinol derivative selected from the group consisting of:

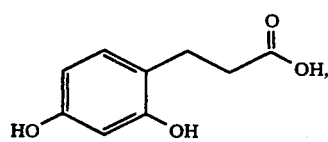
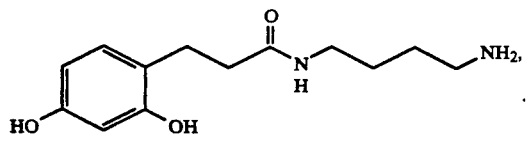
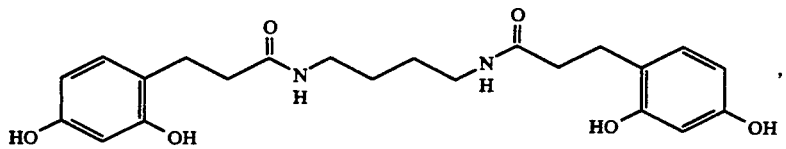
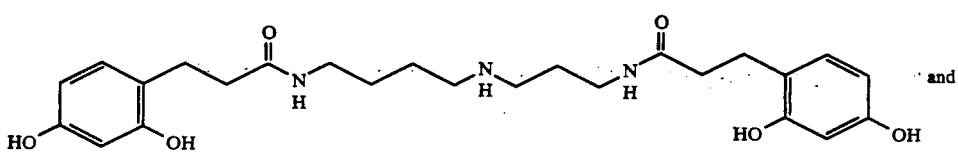 and
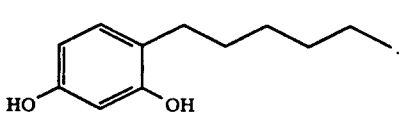

UNITED STATES PATENT AND TRADEMARK OFFICE
CERTIFICATE OF CORRECTION

PATENT NO.   :   5,202,141                               Page 1 of 3
DATED        :   April 13, 1993
INVENTOR(S)  :   McEvily et al.

It is certified that error appears in the above-identified patent and that said Letters Patent is hereby corrected as shown below:

In Claim 1, Column 10, line 34 after "linear" delete ",".

In Claim 7, Column 10, line 54 delete "A" and insert ---The---.

In Claim 8, Column 10, line 57 delete "A" and insert ---The---.

In Claim 13, Column 11, line 13 after "browning of" insert ---the---.

The chemical formulas in Claim 13 and Claim 18, Columns 11 and 12, overlap. Line spacing should be adjusted.

In Claim 20, Column 12, line 53 delete "method" and insert ---composition---.

In Claim 21, Column 12, line 57 delete "method" and insert ---composition---.

In Claim 22, Column 12, line 60 delete "method" and insert ---composition---.

UNITED STATES PATENT AND TRADEMARK OFFICE
CERTIFICATE OF CORRECTION

PATENT NO. : 5,202,141

DATED : April 13, 1993

INVENTOR(S) : McEvily et al.

It is certified that error appears in the above-identified patent and that said Letters Patent is hereby corrected as shown below:

In Claim 23, Column 12, line 63 delete "method" and insert ---composition---.

In Claim 24, Column 12, line 66 delete "A method" and insert ---The composition---.

In Claim 25, Column 13, line 1 delete "A method" and insert ---The composition---.

In Claim 26, Column 13, first line delete "method" and insert ---composition---.

In Claim 27, Column 13, first line delete "method" and insert ---composition---.

In Claim 28, Column 13, first line delete "method" and insert ---composition---.

In Claim 29, Column 13, first line delete "method" and insert ---composition---.

In Claim 36, Column 14, line 59 after "H" delete "," and insert ---or---.

In Claim 36, Column 14, line 61 after "linear" delete ",".

UNITED STATES PATENT AND TRADEMARK OFFICE
CERTIFICATE OF CORRECTION

PATENT NO. : 5,202,141
DATED : April 13, 1993
INVENTOR(S) : Arthur J. McEvily, et al.

It is certified that error appears in the above-indentified patent and that said Letters Patent is hereby corrected as shown below:

Claim 36, column 14, line 61 after "linear" delete ",".

Signed and Sealed this

First Day of February, 1994

*Attest:*

BRUCE LEHMAN

*Attesting Officer*    Commissioner of Patents and Trademarks